US006543535B2

(12) United States Patent
Converse et al.

(10) Patent No.: US 6,543,535 B2
(45) Date of Patent: Apr. 8, 2003

(54) PROCESS FOR STIMULATING MICROBIAL ACTIVITY IN A HYDROCARBON-BEARING, SUBTERRANEAN FORMATION

(75) Inventors: David R. Converse, Houston, TX (US); Stephen M. Hinton, Chester, NJ (US); Glenn B. Hieshima, Houston, TX (US); Robert S. Barnum, Sugar Land, TX (US); Mohankumar R. Sowlay, Phillipsburg, NJ (US)

(73) Assignee: ExxonMobil Upstream Research Company, Houston, TX (US)

( * ) Notice: Subject to any disclaimer, the term of this patent is extended or adjusted under 35 U.S.C. 154(b) by 0 days.

(21) Appl. No.: 09/789,019

(22) Filed: Feb. 20, 2001

(65) Prior Publication Data

US 2001/0045279 A1 Nov. 29, 2001

Related U.S. Application Data

(60) Provisional application No. 60/189,367, filed on Mar. 15, 2000.

(51) Int. Cl.[7] ............................................. E21B 43/22
(52) U.S. Cl. .................... 166/246; 166/268; 166/403
(58) Field of Search .......................... 166/246, 400–403, 166/268; 405/128.45, 128.7; 210/747; 435/262.5, 167

(56) References Cited

U.S. PATENT DOCUMENTS 2,413,278 A   12/1946   Zobell ........................... 195/1

(List continued on next page.)

FOREIGN PATENT DOCUMENTS

| DE | 4036787 A | 5/1992 | |
|---|---|---|---|
| DE | 4115435 C | 8/1992 | |
| DE | 19520548 A | 12/1996 | |
| JP | 09121868 A | 5/1997 | |
| WO | WO 79/00201 | 4/1979 | ........... E21B/43/22 |

OTHER PUBLICATIONS

Anderson, Robert T., and Lovley, Derek R., Hexadecane Decay by Methanogenesis, Nature, v. 404, p. 722, Apr. 13, 2000.

Anderson, Robert T., Rooney–Varga, Juliette N., et al., Anaerobic Benzene Oxidation in the Fe(III) Reduction Zone of Petroleum–Contaminated Aquifers, Environmental Science & Technology, v. 32, pp. 1222–1229, 1998.

(List continued on next page.)

*Primary Examiner*—William Neuder
*Assistant Examiner*—Zakiya Walker
(74) *Attorney, Agent, or Firm*—Gary D. Lawson (57) ABSTRACT

A process is disclosed for stimulating the activity of microbial consortia in a subterranean formation to convert hydrocarbons to methane, which can be produced. Fluid and rock of the formation are analyzed. The presence of microbial consortia is determined and a characterization made (preferably genetic) of at least one microorganism of the consortia, at least one being a methanogenic microorganism. The characterization is compared with at least one known characterization derived from a known microorganism having one or more known physiological and ecological characteristics. This information, together with the information obtained from the analysis of the fluid and rock, is used to determine an ecological environment that promotes in situ microbial degradation of formation hydrocarbons and promotes microbial generation of methane by at least one methanogenic microorganism of the consortia. This information is then used as the basis for modifying the formation environment to produce methane.

37 Claims, 2 Drawing Sheets

U.S. PATENT DOCUMENTS

| | | | |
|---|---|---|---|
| 2,641,566 A | 6/1953 | Zobell | 195/3 |
| 2,659,659 A | 11/1953 | Schmidl | |
| 2,660,550 A | 11/1953 | Updegraff et al. | 195/3 |
| 2,807,570 A | 9/1957 | Updegraff | 195/3 |
| 2,907,389 A | 10/1959 | Hitzman | 166/8 |
| 2,975,835 A | 3/1961 | Bond | 166/42 |
| 3,006,755 A | 10/1961 | Adams | |
| 3,185,216 A | 5/1965 | Hitzman | 166/42 |
| 3,332,487 A | 7/1967 | Jones | 166/11 |
| 3,340,930 A | 9/1967 | Hitzman | 166/9 |
| 3,437,654 A | 4/1969 | Dix | |
| 3,637,686 A | 1/1972 | Kokubo et al. | |
| 3,640,846 A | 2/1972 | Johnson | 195/27 |
| 3,724,542 A | 4/1973 | Hamilton | 166/246 |
| 3,800,872 A | 4/1974 | Friedman | 166/270 |
| 3,826,308 A | 7/1974 | Compere-Whitney | 166/246 |
| 3,982,995 A | 9/1976 | Yen et al. | 195/3 |
| 4,184,547 A | 1/1980 | Klass et al. | 166/246 |
| 4,300,632 A | 11/1981 | Wilberger et al. | 166/246 |
| 4,349,633 A | 9/1982 | Worne et al. | 435/281 |
| 4,358,535 A | 11/1982 | Falkow et al. | 435/5 |
| 4,358,537 A | 11/1982 | Chynoweth | 435/162 |
| 4,386,159 A | 5/1983 | Kanai | 435/167 |
| RE31,347 E | 8/1983 | Reijonen et al. | 48/197 |
| 4,416,332 A | 11/1983 | Wiberger et al. | 166/246 |
| 4,446,919 A | 5/1984 | Hitzman | 166/246 |
| 4,450,908 A | 5/1984 | Hitzman | 166/246 |
| 4,475,590 A | 10/1984 | Brown | 166/246 |
| 4,481,293 A | 11/1984 | Thomsen et al. | 435/167 |
| 4,522,261 A | 6/1985 | McInerney et al. | 166/246 |
| 4,610,302 A | 9/1986 | Clark | 166/246 |
| 4,640,767 A | 2/1987 | Zajic et al. | 208/390 |
| 4,678,033 A | 7/1987 | Killough | 166/246 |
| 4,799,545 A | 1/1989 | Silver et al. | 166/246 |
| 4,826,769 A | 5/1989 | Menger | 435/167 |
| 4,845,034 A | 7/1989 | Menger et al. | 435/167 |
| 4,883,753 A | 11/1989 | Belaich et al. | 435/167 |
| 4,905,761 A | 3/1990 | Bryant | 166/246 |
| 4,906,575 A | 3/1990 | Silver et al. | 435/253.6 |
| 4,914,024 A | 4/1990 | Strandberg et al. | 435/41 |
| 4,947,932 A | 8/1990 | Silver et al. | 166/246 |
| 4,971,151 A | 11/1990 | Sheehy | 166/246 |
| 5,044,435 A | 9/1991 | Sperl et al. | 166/246 |
| 5,076,927 A | 12/1991 | Hunter | 210/603 |
| 5,083,610 A | 1/1992 | Sheehy | 166/246 |
| 5,083,611 A | 1/1992 | Clark et al. | 166/246 |
| 5,087,558 A | 2/1992 | Webster, Jr. | 435/5 |
| 5,100,553 A | 3/1992 | Nomura et al. | 210/610 |
| 5,163,510 A | 11/1992 | Sunde | 166/246 |
| 5,297,625 A | 3/1994 | Premuzic et al. | 166/246 |
| 5,327,967 A | 7/1994 | Jenneman et al. | 166/246 |
| 5,340,376 A | 8/1994 | Cunningham | 71/6 |
| 5,341,875 A | 8/1994 | Jenneman et al. | 166/246 |
| 5,350,684 A | 9/1994 | Nakatsugawa et al. | 435/167 |
| 5,360,064 A | 11/1994 | Jenneman et al. | 166/246 |
| 5,363,913 A | 11/1994 | Jenneman et al. | 166/246 |
| 5,368,099 A | 11/1994 | Davey et al. | 166/246 |
| 5,424,195 A | 6/1995 | Volkwein | 435/34 |
| 5,492,828 A | 2/1996 | Premuzic et al. | 435/245 |
| 5,500,123 A | 3/1996 | Srivastava | 210/603 |
| 5,510,033 A | 4/1996 | Ensley et al. | 210/611 |
| 5,516,971 A | 5/1996 | Hurley | |
| 5,538,530 A | 7/1996 | Heaton et al. | |
| 5,551,515 A | 9/1996 | Fodge et al. | 166/300 |
| 5,560,737 A * | 10/1996 | Schuring et al. | 405/128.45 |
| 5,593,886 A | 1/1997 | Gaddy | 435/252.7 |
| 5,630,942 A | 5/1997 | Steiner | 210/603 |
| 5,670,345 A | 9/1997 | Srivastava et al. | 435/75 |
| 5,695,641 A | 12/1997 | Cosulich et al. | 210/603 |
| 5,723,597 A | 3/1998 | Kohne | 536/24.3 |
| 5,763,736 A | 6/1998 | Daume | |
| 5,858,766 A | 1/1999 | Premuzic et al. | 435/262.5 |
| 5,885,825 A | 3/1999 | Lin et al. | 435/262.5 |
| 5,919,696 A | 7/1999 | Ikeda et al. | 435/262.5 |
| 5,928,864 A | 7/1999 | Kohne | 435/6 |
| 5,955,261 A | 9/1999 | Kohne | 435/5 |
| 5,955,262 A | 9/1999 | Kourilsky et al. | 435/6 |
| 6,090,593 A | 7/2000 | Fleming et al. | 435/91.2 |
| 6,265,205 B1 * | 7/2001 | Hitchens et al. | 435/262 |

OTHER PUBLICATIONS

Artech Inc., Biological Gasification of Coals. Final Report, U.S. Department of Energy, Contract DE–AC21–87MC23285, pp. 40–63, 1990.

Brown, L.R., and Vadie, A.A., et al., Slowing Production Decline and Extending the Economic Life of an Oil Field: New MEOR Technology, SPE 59306; SPE/DOE Improved Oil Recovery Symposium, Tulsa, Oklahoma, Apr. 3–5, 2000.

Coates, John D., Anderson, Robert T., et al., Anaerobic Hydrocarbon Degradation in Petroleum–Contaminated Harbor Sediments under Sulfate–Reducing and Artificially Imposed Conditions, Environ. Sci. Technol., vol. 30, No. 9, pp. 2784–2789, 1996.

Donaldson, Eric C., Chilingarian, George V., and Yen, Teh F., Microbial Enhanced Oil Recovery, Developments in Petroleum Science, v. 22, pp. 1–27, 1989.

Gullapalli, Irene L., Bae, Jae H., et al., Laboratory Design and Field Implementation of Microbial Profile Modification Process, SPE Reservoir Evaluation & Engineering, v. 3, No. 1, pp. 42–49, Feb. 2000.

L'Haridon, S., Reysenbach, A.L., et al., Hot Subterranean Biosphere in a Continental Oil Reservoir, Nature, v. 377, pp. 223–224, Sep. 21, 1995.

Le Blanc, Leonard, Artificial Recharge, Offshore, p. 10, Feb. 2000.

Magot, Michel, Ollivier, Bernard, and Patel, Bharat K.C., Microbiology of Petroleum Reservoirs, Antonie Van Leeuwenhoek, v. 77, pp. 103–116, 2000.

Panow, A., FitzGerald, J.M.P., and Mainwaring, D.E., Mechanisms of Biologically–Mediated Methane Evolution from Black Coal, Fuel Processing Technology v. 52, pp. 115–125, 1997.

Rooney–Varga, Juliette N., Anderson, Robert T., Fraga, et al., Microbial Communities Associated with Anaerobic Benzene Degradation in a Petroleum–Contaminated Aquifer, Applied and Environmental Microbiology, v. 65, No. 7, pp. 3056–3063, Jul. 1999.

Rozanova, E.P., Borzenkov, I. A., et al., Microbiological Processes in a High–Temperature Oil Field, Microbiology, v. 70, No. 1, pp. 102–110, 2000.

Volkwein, J.C., Schoeneman, A.L., et al., Biological Production of Methane from Bituminous Coal, Fuel Processing Technology, v. 40, pp. 339–345, 1994.

Belyaev, S. S., Wolin, R., Kenealy, W. R., and others, 1983, Methanogenic Bacteria from the Bondyuzhskoe Oil Field: General Characterization and Analysis of Stable–Carbon Isotopic Fractionation: Applied and Environmental Microbiology, v. 45, No. 2, pp. 691–697.

Bernard, F. P., Connan, J., and Magot, M., 1992, Indigenous Microorganisms in Connate Water of Many Oil Fields: A New Tool in Exploration and Production Techniques: SPE 24811, pp. 467–476.

Connan, J., Lacrampe–Couloume, G., and Magot, M., 1996, Origin of Gases in Reservoirs: 1995 International Gas Research Conference pp. 21–41.

Connan, J., Lacrampe–Couloume, G., and Magot, M., 1997, Anaerobic biodegradation of petroleum in reservoirs: a widespread phenomenon in nature: 18th International Meeting on Organic Geochemistry Sep. 22–26, 1997 Maastricht, The Netherlands (Abstr.), p. O2: 5–6.

Grbic–Galic, D., and Vogel, T., 1987, Transformation of Toluene and Benzene by mixed methanogenic cultures: Applied and Environmental Microbiology, v. 53, pp. 254–260.

Groudeva, V. I., Ivanova, I. A., Groudev, S. N., and others, 1993, Enhanced Oil Recovery by Stimulating the Activity of the Indigenous Microflora of Oil Reservoirs: Biohydrometallurgical Technologies (Eds. Torma, A. E., Apel, M.L.; and Brierlay, C.L.): Minerals, Metals, & Mater. Soc. Biohydromet. Technol. Int. Symp (Jackson Hole, Wy. 93.8.22–25) Proc., v. 2, pp. 349–356.

Halbouty, M.T., 1991 East Texas Field—USA, East Texas Basin, Texas; in Stratigraphic Traps II (compiled by N.H. Foster, and E.A. Beaumont) AAPG Treatise of Petroleum Geology, Atlas of Oil and Gas Fields pp. 189–206.

Hales, B.A., Edwards, C., Ritchie, D.A., Hall, G., Pickup, R.W., Saunders, J.R., 1996, Isolation and Identification of Methanogen–specific DNA from Blanket Bog Peat by PCR Amplification and Sequence Analysis, Applied and Environmental Microbiology, 668–675.

Hermann, M., Vandecasteel, J–P., and Ballerini, D., 1992, Anaerobic Microflora of Oil Reservoirs: Microbiological Characterization of Samples from Some Production Wells: Bacterial Gas (R. Vially Ed.) Editions Technip. Paris, pp. 223–233.

Ivanov, M. V., Belyaev, S. S., Borzenkov, I. A., and others, 1993, Additional Oil Production During Field Trials in Russia: Microbial Enhancement of Oil Recovery—Recent Advances (4th US DOE MEOR Int Conf (Upton, NY, 1992) Proc; Elsevier Develop Petrol Sci Ser No. 39), pp. 373–381.

Ivanov, M. V., Beljaev, S. S., Zjakun, A. M., and others, 1982, Die mikrobiologische Bildung von Methan in einer abzubauenden Erdollagerstatte; Frieberger Forschungshefte Reihe C, v. vol. 389, pp. 189–199.

Klein, A., Allmansberger, R., Bokranz, M., Knaub, S., Muller, B, and Muth, E., 1988, Comparative Analysis of Genes Encoding Methyl Coenzyme M Reductase in Methanogenic Bacteria, Mol Gen Genet, 213:409–420.

Li, M., Zhang, H. Liu H., Zhang, H., and others, 1996, Advances in Simulated Tests of Biogas: Oil & Gas Geology, v. vol. 17, No. 2, pp. 117–122.

McDonald, I.R., Upton, M., Hall, G., Pickup, R.W., Edwards, C., Saunders, J.R., Ritchie, D.A., Murrell, J.C., 1999, Molecular Ecological analysis of Methanogens and Methanotrophs in Blanket Bog Peat, Microb Ecol, 38(3):225–233.

Nazina, T. N., Ivanova, A. E., Borzenkov, I. A., and others, 1995, Occurrence and Geochemical Activity of Microorganisms in High–Temperature, Water–Flooded Oil Fields of Kazakhstan and Western Siberia: Geomicrobiology Journal, v. 13, pp. 181–192.

Nazina, T. N., Rozanova, E. P., and Kuznetsov, S. I., 1985, Microbial Oil Transformation Processes Accompanied by Methane and Hydrogen–Sulfide Formation: Geomicrobiology Journal, vol. 4, No. 2, pp. 103–130.

Ng, T. K., and Weimer, P. J., 1989, Possible Nonanthropogenic Origin of Two Methanogenic Isolates from Oil–Producing Wells in the San Miguelito Field, Ventura County, California: Geomicrobiology Journal, v. 7, pp. 185–192.

Revesz, K., Coplen, T. B., Baedecker, M. J., and others, 1995, Methane production and consumption monitored by stable H and C isotope ratios at a crude oil spill site, Bemidji, Minnesota: Applied Geochemistry, vol. 10, pp. 505–515.

Springer, E., Sachs, M.S., Woese, C.R., Boone, D.R., 1995, Partial Gene Sequences for the A Subunit of Methyl–Coenzyme M Reductase (McrI) as a Phylogenetic Tool for the Family Methanosarcinaceae, International Journal of Systematic Bacteriology, 554–559.

Weiner, J. M., and Lovley, D. R., 1998, Rapid Benzene Degradation in Methanogenic Sediments from a Petroleum–Contaminated Aquifer: Appl. Environ. Microbiology v. vol. 64, No. 5, pp. 1937–1939.

Zengler et al., "Methane Formation From Long–Chain Alkanes by Anaerobic Microorganisms," Nature, vol. 401, pp. 266–269, Sep. 16, 1999.

Hunkeler et al., "Petroleum Hydrocarbon Mineralization in Anaerobic Laboratory Aquifer Columns," Journal of Contaminant Hydrology 32, pp. 41–61, 1998.

Orphan et al., "Culture–Dependant and Culture–Independent Characterization of Microbial Assemblages Associated with High–Temperature Petroleum Reservoirs," American Society for Microbiology, pp. 700–711, 2000.

Donaldson et al., "Microbial Enhanced Oil Recovery," Developments in Petroleum Science 22, pp. 8–12, 121, 123, 149. (undated).

Potter et al. "Artificial Recharge," Offshore, p. 10, Feb. 2000.

Donaldson et al., "Conference Focuses on Microbial Enhancement of Oil Recovery," The Oil and Gas Journal, pp. 47–52, Dec. 20, 1982.

Zobell, C.E., "Bacterial Release of Oil From Sedimentary Materials," The Oil & Gas Journal, pp. 62–65, Aug. 2, 1947.

Chemical Abstracts, vol. 130, No. 5, Feb. 1, 1998, Columbus, Ohio, U.S.; Abstract No. 54464a, R. Flesner et al.: "Pilot–scale base hydrolysis processing of HMX–based plastic–bonded explosives", p. 835; XP000861211.

* cited by examiner

PROCESS FOR STIMULATING MICROBIAL ACTIVITY IN A HYDROCARBON-BEARING, SUBTERRANEAN FORMATION

CROSS-REFERENCE

This application claims the benefit of U.S. Provisional Application No. 60/189,367, filed Mar. 15, 2000.

FIELD OF THE INVENTION

This invention relates generally to a process of using microorganisms to convert hydrocarbons (liquids, solids, and gases) to methane and other gases in a subterranean formation.

BACKGROUND

When oil is present in subterranean rock formations such as sandstone, carbonate, chert or shale, it can generally be exploited by drilling into the oil-bearing formation and allowing existing pressure gradients to force the oil up the borehole. This process is known as primary recovery. If and when the pressure gradients are insufficient to produce oil at the desired rate, it is customary to carry out an improved recovery method to recover additional oil. This process is known as secondary recovery.

There are several secondary recovery techniques, including gas injection and water injection. Choice of a specific secondary recovery technique depends on the specifics of the hydrocarbon accumulation. Water injection or waterflooding is the most common secondary recovery technique. In waterflooding, pressurized water is injected into the oil-bearing formation and produced from neighboring hydrocarbon production wells. First hydrocarbon, and subsequently hydrocarbon and water are recovered from the production well.

However, even after secondary recovery, a significant portion of hydrocarbon remains in the formation, in some cases up to 75% of the original hydrocarbon in place. The fraction of unrecoverable hydrocarbon is typically highest for heavy oils, tar, and complex formations. In large oil fields, more than a billion barrels of oil can be left after conventional waterflooding. Much of this remaining oil is in micro-traps due to capillary forces or adsorbed onto mineral surfaces (irreducible oil saturation) as well as bypassed oil within the rock formation. One enhanced oil recovery technique uses microorganisms such as bacteria to dislodge the micro-trapped or adsorbed oil from the rock. The goal of this technique, which is known as microbially enhanced oil recovery (MEOR), is to increase oil recovery of the original subsurface hydrocarbons. MEOR processes typically use microorganisms to: (1) alter the permeability of the subterranean formation, (2) produce biosurfactants which decrease surface and interfacial tensions, (3) mediate changes in wettability, (4) produce polymers which facilitate mobility of petroleum, (5) produce low molecular weight acids which cause rock dissolution, and (6) generate gases (predominantly $CO_2$) that increase formation pressure and reduce oil viscosity.

Numerous microorganisms have been proposed for achieving various microbial objectives in subterranean formations. Most MEOR techniques involve injection and establishment of an exogenous microbial population into the oil-bearing formation. The population is supplied with nutrients and mineral salts as additives to the waterflood used for secondary oil recovery. The development of exogenous microorganisms has been limited by the conditions that prevail in the formation. Physical constraints, such as the small and variable formation pore sizes together with the high temperature, salinity and pressure of fluids in the formation and the low concentration of oxygen in the formation waters severely limit the types and number of microorganisms that can be injected and thrive in the formation. Biological constraints, such as competition from indigenous microbes and the stress of changing environments (from surface to subsurface) also act to limit the viability of exogenous microorganisms. To overcome these problems, indigenous microorganisms, commonly anaerobic, have been proposed in MEOR projects.

In addition to MEOR activities, microorganisms have also been proposed for making methane from fossil fuel deposits. Recent studies have demonstrated that hydrocarbons can be converted by microbial processes to methane. Patents proposing this concept include U.S. Pat. No. 3,826,308 (Compere-Whitney), which used microorganisms to produce methane from fossil fuel deposits containing organic ring compounds; U.S. Pat. No. 5,424,195 (Volkwein) which converted coal to methane in situ using a consortium of exogenous microorganisms (developed in a coal-bearing cavity); and U.S. Pat. Nos. 4,845,034 and 4,826,769 by Menger et al. which pretreated subterranean cavities having finely-divided carbonaceous material with an aqueous alkali solution and then biochemically reacted the carbonaceous material with either exogenous or indigenous methane-producing microorganisms to produce methane. The prior art does not suggest how to identify specific microorganisms of the indigenous microbial community for the purpose of determining processes for stimulating and sustaining microbial activity to degrade hydrocarbons and generate methane. The prior art also does not suggest developing a practical ecological model to determine processes for stimulating and sustaining in situ microbial activity.

With appropriate environmental conditions and sufficient time, indigenous bacteria can convert hydrocarbons to methane. However, such a natural process may require residence times of hundreds to millions of years. The conversion process is apparently slow under most geological conditions. The problem to be solved is to find a process of accelerating and sustaining biochemical conversion of hydrocarbons to methane at a rate that is commercially practical or establishing and/or maintaining an in situ environment that supports commercial rates of hydrocarbon conversion and methanogenesis.

SUMMARY

This invention relates to a process of stimulating the activity of microbial consortia in a hydrocarbon-bearing, subterranean formation to convert hydrocarbons to methane and other hydrocarbon gases, which can be produced. The hydrocarbons can be carbonaceous deposits in solid, liquid, or gaseous form such as coal, oil shale, tar sands, oil formations, and rich gas or the hydrocarbons can be unwanted subsurface hydrocarbons of a hydrocarbon reclamation project. An analysis is made of the environmental conditions in the formation, preferably by obtaining samples of formation fluid and/or rock and then analyzing the samples. The presence of microbial consortia in the formation is determined, preferably by analyzing one formation samples for the presence of microorganisms in the samples. A characterization, preferably a genetic characterization, is made of at least one microorganism of the consortia, at least one of which is a methanogenic microorganism, and comparing said characterization with at least one known characterization, preferably a genetic characterization, derived from a known microorganism having one or more known ecological characteristics. This information, together with the information obtained from the analysis of the fluid and rock, is used to determine an ecological environment that promotes in situ microbial degradation of formation hydrocarbons and promotes microbial generation of methane by at least one methanogenic microorganism of the consortia. This ecological information is then used as the basis for modifying the formation environment to stimulate and sustain microbial conversion of formation hydrocarbons to methane. The formation environment can be modified by carrying out at least one of the following stimulation techniques: (1) adding, subtracting, and/or maintaining components needed for microbial growth, and/or (2) controlling and/or maintaining formation environmental factors such as chemistry, temperature, salinity, and pressure.

BRIEF DESCRIPTION OF THE DRAWINGS

The invention and its advantages will be better understood by referring to the drawings which are not necessarily to scale and in which.

DETAILED DESCRIPTION

The process of this invention stimulates and sustains the activity of a mixture of different microorganisms in a hydrocarbon-bearing, subterranean formation to convert hydrocarbons to methane and other gases, which can be produced. While not wishing to be held to any specific theory, it is believed that a mixture of microorganisms converts hydrocarbons to methane in multiple acts as follows:

(1) Microbial consortia degrade various hydrocarbon compounds (e.g., saturated, aromatic, asphaltenic, and nitrogen-sulfur-oxygen bearing compounds) by a single act or a series of acts into various compounds, which may include amines, alcohols, organic acids, and gases.

(2) Methanogens convert various compounds, which may include amines, alcohols, organic acids, and gases, into methane, $CO_2$, and water.

The microorganisms naturally present in a subterranean formation will typically involve multiple, mixed consortia of microorganisms, which will often depend on each other. For example, in the degradation of hydrocarbons, syntrophic hydrogen-producing microorganisms obtain energy from hydrocarbon degradation if their metabolic waste products (such as organic acids, acetate, and $H_2$) are continuously removed and kept at a relatively low concentration. Methanogenic microorganisms perform part of this waste-removal function by converting at least some of the waste products (for example, acetate, $CO_2$ and $H_2$) to methane and other low molecular weight hydrocarbons such as ethane.

Figure 1:
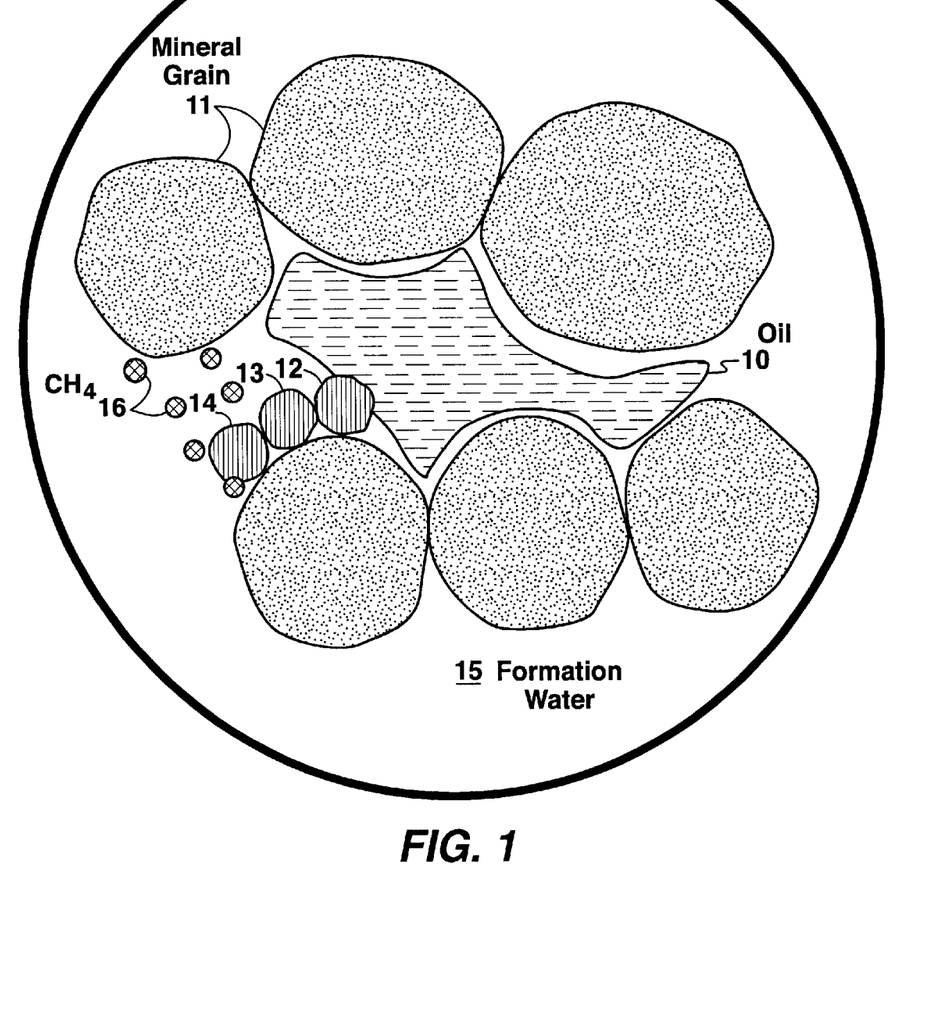
FIG. 1 is a schematic representation of rock grains of an oil-bearing formation showing oil and water between the rock grains and microorganisms that are converting at least part of the oil to methane.

FIG. 1 schematically illustrates one example of oil to methane conversion by at least one microbial consortium. FIG. 1 schematically illustrates rock grains of an oilbearing formation showing oil 10 between the rock grains 11 and microorganisms 12, 13, and 14 that are in the process of converting oil to methane. Oil 10 in pore spaces between mineral grains 11 is attacked by a first microbe 12 (which could for example be a fermenter) that converts at least part of oil 10 to organic acids and other intermediate compounds (not shown). This first microbe 12 may be in direct contact with the oil 10, it may be attached to the mineral grains 11, or it may be suspended in the formation water 15. The products of the first microbe 12 may be processed by a second microbe 13 to produce smaller organic acids (not shown) including acetate, $CO_2$, $H_2$, and other compounds. The last act in this example process converts $CO_2$, acetate, $H_2$ and other compounds to methane 16 by a third microbe 14. The microbes 12, 13, and 14 may be in direct contact with each other or may be separated.

This description of one embodiment of the invention will focus on converting hydrocarbons to methane in a conventional oil-bearing formation. However, the process of this invention can be applied to any hydrocarbon-bearing formation in which environmental conditions can be modified to stimulate growth of at least one hydrocarbon-degrading microorganism and of at least one microorganism that is capable of converting the degraded products to methane. The process of this invention can be used to stimulate microbial activity in oil shale deposits, coal, tar sands and other fossil fuel deposits to transform the hydrocarbons contained therein to methane. As used in this description, the term "hydrocarbons" is used in a broad sense to include solid carbonaceous deposits such as kerogen, peat, lignite, and coal; liquid carbonaceous deposits such as oil; gaseous hydrocarbons; and highly viscous carbonaceous deposits such as bitumen and tar.

This process of the invention can also be applied to reclamation projects where hydrocarbon-contaminated soils and aquifers can be treated to enhance microbial conversion of hydrocarbons to recoverable methane and other hydrocarbon gases.

In this description, indigenous microorganisms are identified and then stimulated to transform hydrocarbons to methane. Microorganisms naturally present in the formation are preferred because it is known that they are capable of surviving and thriving in the formation environment. However, this invention is not limited to use of indigenous microorganisms. Exogenous microorganisms suitable for growing in the subterranean formation may be introduced into the formation by known injection techniques before, during, or after practicing the process of this invention. For example, if the formation contains only two microorganisms of a desired three-component consortia, then the missing microorganisms could be injected into the formation before practicing the present invention. Alternatively, the missing microorganisms could be injected into the formation as the formation environment is being modified to promote growth of microbial consortia. In another embodiment, all of the microorganisms used for converting the hydrocarbons to methane could be exogenous. In still another embodiment, mutations of indigenous microorganisms could be developed in a laboratory and injected into the formation.

In this patent, reference to "microorganisms" is intended to include bacteria and archaea organisms, their enzymes, and other products as well as related fungi and molds. It will be understood that bacteria and archaea are representative of microorganisms in general that can degrade hydrocarbons and convert the resulting products to methane. The dividing lines between classes of microorganisms are not always distinct, particularly between bacteria and fungi. It is preferred, therefore, to use the term microorganisms to include all microbial consortia that can convert hydrocarbons in the formation to methane, whatever the commonly used classifications might be. Of these microorganisms, those usually classified as bacteria and archaea are, however, preferred. If exogenous bacteria and archaea are used as the source of bacteria and archaea, other microorganisms such as fungi, yeasts, molds, and the like can also be present. Some of these may, and probably will, be carried through development cultures and may be introduced into the formation. Therefore, the term microorganisms as used in this description is not necessarily limited to bacteria and archaea.

Step 1: Analyzing the Fluid/rock Chemistry and Microbiology

In practicing the process of this invention, the first step is to analyze one or more samples of fluids and rocks in the hydrocarbon-bearing formation in which microbial activity is to be stimulated. While one sample is sufficient to practice the invention, multiple samples may be obtained.

Collecting Samples

The samples can be obtained by sampling procedures that are known to those skilled in the art. Normally, a fluid or gas sample is retrieved from the formation through perforations in a well casing or from an open-hole test. The fluids can be sampled either downhole with a wireline formation fluid tester or fluid sampler or at the surface wellhead from a subsurface test, such as drill stem tests, production tests, or normal production. Both formation water and hydrocarbon samples are useful for evaluation of the formation environment. Rock samples can be retrieved from drill cores, cuttings, produced sediments (including bailed samples) and/or outcrop sites or rock data can be secured by interpretation of well logs.

Environmental Analysis

An analysis of the formation's environment provides useful information in determining suitable microbial growth stimulants or in situ environmental conditions for microbial growth. This analysis preferably includes determining the formation's temperature and pressure, which can be obtained in any suitable manner. A geochemical analysis can be made of one or more fluids of the formation, such as formation water and hydrocarbons, and/or one or more solids of the formation, which analyses are familiar to those skilled in the art. Preferably, the analysis is made of fluid and/or rock samples obtained from the formation. The fluid analysis can include measurement of the state values (for example, temperature and pressure) as well as a geochemical analysis of the formation water which can include assay for pH, oxidation potential (Eh), phosphorous, nitrate, ammonia, sulfate, salinity, selenium, molybdenum, cobalt, copper, nickel, and other trace metals. The geochemical analysis will preferably also identify by-products that are known to be produced by indigenous microbial activity. For example, presence of methane, $CO_2$, enzymes, and carboxylic acids can be indicative of microbial activity. Hydrocarbon analyses of oil and gas will aid in identifying the abundances and compositions of the different carbon substrates for the microorganisms. The rock analysis may include mineralogical, chemical and facies descriptions as well as measurements of formation properties such as porosity, permeability, capillary pressure, and wettability.

Microbial Analysis

Collecting Indigenous Microorganisms

The sample, which most commonly will be formation water and/or a rock sample, is directly analyzed for the presence of microorganisms. The microorganisms are preferably concentrated by filtration and/or centrifugation before the analysis is performed. The amount of the indigenous microbe population will typically be a small fraction of the sample's volume. In a typical oil-bearing formation, water may contain less than 0.025 mg of microorganisms per liter. Alternatively, the indigenous microorganisms can be first cultured in the laboratory using techniques familiar to those skilled in the art and then concentrated and collected. Microorganism concentrations can be amplified to facilitate detection using conventional microbial detection techniques, which are familiar to those skilled in the art.

Characterizing the Indigenous Microorganisms

Microorganism characterization as used in this description means identifying the key characteristics of a microorganism or consortium of microorganisms using one or more of the following methods: biochemical methods, physiological methods, morphological methods, or genetic methods. The degree of similarity between these key characteristics of sampled microorganism and the known microorganism can be used to establish identity and infer the physiology, metabolic functions, and ecological traits of the sampled microorganisms by techniques well established in the field of microbial ecology (for example, see Stahl, D. A., "Chapter 11: Molecular Approaches for the measurement of density, diversity, and phylogeny", Manual of Environmental Microbiology (editors C. J. Hurst; G. R. Knudsen, M. J. McInerney, L. D. Stetzenbach, M. V. Walker), ASM press, Washington D.C., 1997, pp. 102–114; Truper, H. G. and Schleifer, K-H., "Chapter 5: Prokaryote Characterization and Identification" in The Prokaryotes, Second Edition, (eds., A. Balows, H. G. Truper, M. Dworkin, W. Harder, K-H. Schleifer) 1992 Vol 1, pp. 126–148).

Nonlimiting examples of characterization methods that can be used in the process of the invention include:

Enrichment culture techniques to obtain microorganism isolates from which key biochemical, morphological, physiological, ecological, and genetic traits may be determined and compared against the traits of known microorganisms.

Determination of the polar lipid fatty acid composition (PLFA) of the microorganisms and comparison with PLFA distributions of known microorganisms.

Genetic characterization methods, of which two non-limiting examples (among many) are listed below:
1. Sequences of genetic fragments from sampled microorganisms including but not restricted to 16S rDNA (bacterial, archaeal) and methanogen-specific mcrA genes) are compared against genetic sequences from known microorganisms (for example, the Genbank database at the National Center for Biotechnology Information located in the National Library of Medicine (Building 38A Room 8N805), Bethesda, Md. 20894, U.S.A.) to establish the phylogenetic identity with nearest known relatives using techniques known to one skilled in the art.
2. Genetic probes that are designed to hybridize or anneal to the DNA of specific microorganisms. The probes can be either unlabeled or labeled with radioactive, biotin, fluorescent and other suitable tags. Specific binding of a DNA probe with a region of denatured genomic DNA indicates the presence or absence of a target nucleic acid and hence the identity of microbe present can be inferred.

The following paragraphs describe an application of DNA probes to identify the presence and identity of methanogens. This description will aid the reader in the basic understanding of one technique for detecting the presence of microorganisms, which is then followed by a technique for DNA sequencing and microbe identification.

a. Determining the presence and identity of methanogens:

The conversion of hydrocarbons to methane requires the active participation of methanogens. The presence of methanogens within the samples indicates the high likelihood of in situ methane formation. A DNA probe can be developed by those skilled in the art to detect the presence of genes that are unique and omnipresent in methanogenic microorganisms. A preferred DNA probe to detect the presence of very small numbers of methanogens is described below. Application of this probe aids in determining viability of methanogenesis in the formation.

Methanogens are typically classified into four major groups of microorganisms: Methanobacteriales, Methanomicrobacteria and relatives, Methanopyrales and Methanococcales. All methanogenic microorganisms are believed to employ elements of the same biochemistry to synthesize methane. Methanogenesis is accomplished by a series of chemical reactions catalyzed by metal-containing enzymes. One pathway is to reduce $CO_2$ to $CH_4$ by adding one hydrogen atom at a time. Another pathway is the fermentation of acetate and single-carbon compounds (other than methane) to methane. The last step in all known pathways of methanogenesis is the reduction of a methyl group to methane using an enzyme known as methyl reductase. As the presence of methyl reductase is common to all methanogens; it is a definitive character of methanogenic microorganisms. The preferred method for identifying the presence of methanogens is to test directly for the methanogen gene (the DNA genetic code) required to produce the methyl reductase enzyme. Alternatively the presence of methanogens can be determined by comparison of the recovered 16S rDNA against an archaeal 16S rDNA library using techniques known to one skilled in the art.

DNA Probing for the Methyl Reductase Gene

The methyl reductase enzyme is composed of a complex of three proteins, labeled the $\alpha$, $\beta$, and $\delta$ subunits, which are encoded for in the methanogens' DNA by three methyl reductase genes, mcrA, mcrB and mcrG, respectively. The preferred DNA detection method focuses on the mcrA gene. Methyl reductase gene sequences from the four major groups of methanogens can be obtained from a gene database (for example, the Genbank database).

The methyl reductase protein sequences can be deduced by translating the methanogen DNA sequence encoded by the mcrA gene into amino acid sequences. A comparison of the amino acid sequences of the methyl reductase alpha subunits from various methanogens reveals several segments in the amino acid sequences that are highly similar. These regions are conserved because they form the actual chemical structures required for the enzyme's function; therefore they are called structure-function domains.

The preferred DNA detection method for the methyl reductase gene uses two specific structure-function domains from the mcrA gene and polymerase chain reaction (PCR) technology. PCR technology mimics the natural process of DNA replication to repetitively synthesize large numbers of specific DNA regions. In this method, the PCR reaction is initiated by oligonucleotide primers that are complementary to two structure-function domains of methyl reductase amino acid sequence found only in the methyl reductase enzyme. If a mcrA gene or multiple mcrA genes from different organisms are present, only then will their numbers be amplified, a million-fold or more, yielding a sufficient quantity for analysis. The products of the PCR reaction are mcrA gene fragments containing both probe sequences at their respective ends and the intervening sequence. Both structure-function domains must be present for a PCR amplification reaction to be a positive test for the presence of methanogenic DNA.

b. Characterizing methanogens by sequencing the mcrA gene

The unique sequence in the intervening region can then be used to identify which methanogen produced the mcrA genes. The DNA sequence of the amplified fragment of the methyl reductase gene is determined (as discussed below) and compared to known DNA sequences to verify the PCR results and infer the identity of the organism that produced the mcrA gene.

Analysis and identification of more than just the methanogens are helpful in understanding the ecology and chemistry of the entire process of microbial degradation of hydrocarbons and the formation of methane. A preferred process to identify genetically subsurface microorganisms follows.

c. Characterization of subsurface microorganisms

As the hydrocarbon-degrading process and methanogenesis involve multiple microbial species, identification of the active microorganisms in the consortia is important. Many of the sampled microorganisms will be unknown species but with known genetic relatives. This information can provide insight into the nutritional needs of the microbial consortia, which will assist in formulation of a stimulant package.

In a preferred identification technique, the DNA from the entire microbial community is first isolated and then amplified using gene-specific primers (commonly 16S universal primers) and PCR technology. Next the fragments are purified by a number of techniques and then ligated into molecular vehicles (for example, plasmid DNA) and transformed into bacteria (usually *E. coli*) as part of the cloning process to create large numbers of isolated DNA fragments. Cultures of individual bacterial colonies are used to isolate individual clones (recombinant plasmid DNA) and then these clones are sequenced using target specific primers. The resultant DNA sequences are then compared with known strains of DNA sequences in molecular gene databases. In most cases, the identities of the microorganisms can be inferred if there are close matches to known microorganisms having known physiological and ecological characteristics. Such identification techniques are known to those skilled in the art. See for example, Nilsen, R. K, and Torsvik, T., "*Methanococcus thermolithotrophicus Isolated from North Sea Oil Field Reservoir Water,*" Applied and Environmental Microbiology, v. 62, pg. 728–731, 1996.

Step 2: Determining How to Stimulate Commercial Rates of Hydrocarbon Degradation and Methanogenesis From knowledge of the indigenous microorganisms and their nutritional requirements, the chemical composition of the formation's oil and water and matrix rock, and the physical characteristics of the formation (pressure, temperature, porosity, saturation, etc.), the overall ecological environment needed to promote and/or sustain the activity of the microbial consortia can be determined. This information is then used to modify the formation's environmental parameters to promote microbial conversion of hydrocarbons to methane.

Stimulating and sustaining high levels of microorganism activity in the subsurface depends on at least one of the following factors:

1) Adding and/or subtracting and/or maintaining key components for microbial growth as determined by the microbial ecology or laboratory and/or in situ pilot studies; and 2) Controlling and/or maintaining the subsurface environment (for example, chemistry, temperature, salinity, and pressure).

Microbial Ecology

In order to stimulate and/or sustain commercial rates of hydrocarbon degradation and methane generation, basic components of the subsurface microbial ecology are determined. To convert hydrocarbons to methane, the formation's indigenous microbial consortia may comprise hydrocarbon-degrading microorganisms having similar genetic characteristics to one or more of the following microorganisms: Archaeoglobales, Thermotogales, Cytophaga group, Azospirillum group, Paracoccus subgroup, Sphingomonas group, Nitrosomonas group, Azoarcus group, Acidovorax subgroup, Oxalobacter group, Thiobacillus group, Xanthomonas group, Oceanospirillum group, Pseudomonas and relatives, Marinobacter hydrocarbonoclaticus group, Pseudoalteromonas group, Vibrio subgroup, Aeromonas group, Desulfovibrio group, Desulfuromonas group, Desulfobulbus assemblage, Campylobacter group, Acidimicrobium group, Frankia subgroup, Arthrobacter and relatives, Nocardiodes subgroup, Thermoanaerobacter and relatives, Bacillus megaterium group, Carnobacterium group, Clostridium and relatives, and include methanogenic archaea (Methanobacteriales, Methanomicrobacteria and relatives, Methanopyrales, and Methanococcales) to convert degraded products to methane. The premise of this technique is that the ecology of the subsurface microbes can be inferred from the ecology of the nearest genetic relatives and/or laboratory culture experiments.

Understanding the subsurface ecology allows one skilled in the art to deduce likely additives that can stimulate subsurface activity. Additives could include (in an appropriate form for distribution throughout the formation) but are not limited to:

major nutrients containing nitrogen and phosphorus (non-limiting examples may include $NaNO_3$, $KNO_3$, $NH_4NO_3$, $Na_2HPO_4$, $K_2HPO_4$, $NH_4Cl$;

vitamins (non-limiting examples may include folic acid, ascorbic acid, and riboflavin);

trace elements (non-limiting examples may include B, Zn, Cu, Co, Mg, Mn, Fe, Mo, W, Ni, and Se);

buffers for environmental controls;

catalysts, including enzymes; and both natural and artificial electron acceptors (non-limiting examples may include $SO_4^{2-}$, $NO_3^{-2}$, $Fe^{+3}$, humic acid, mineral oxides, quinone compounds, $CO_2$, $O_2$, and combinations thereof For example, if selenium is known to stimulate growth of the closest-matching methanogenic microorganism, and if selenium is present in the formation in only limited concentrations, then addition of selenium to the formation should also stimulate the unknown methanogens.

Suitable stimulants can be tested and optimized using indigenous microorganisms in laboratory cultures or in situ pilot sites to determine their effectiveness at promoting rapid hydrocarbon-degradation and methanogenesis. The indigenous microbial consortia are grown in nutrients using a range of nutrient media, with varying pH, salinity, trace metals, and electron acceptors to find those conditions which support high rates of degradation and methanogenesis. These culture studies will typically involve several cycles of stimulant additives and stimulant combinations as well as environmental conditions (e.g. salinity, temperature, pH—see below). Because the indigenous microorganisms found in a given formation and the chemistry of the formation fluids and formation rocks will typically be unique to that formation, the conditions for promoting growth of indigenous microorganisms may vary from one hydrocarbon accumulation to another and may vary from one location in the hydrocarbon accumulation to another. Conditions favorable for microorganism growth in part of the hydrocarbon accumulation may not be optimum for another part of the hydrocarbon accumulation.

If the formation contains microorganisms that may be harmful to growth of the beneficial microorganisms, environmental conditions in the formation may be altered to suppress growth of the harmful microorganisms. For example, some oil-bearing formations have a sulfate-rich environment and indigenous sulfate-reducing microorganisms (SRB) could out-compete the methanogenic microorganisms, which would be undesirable because less methane would be produced by methanogenic microorganisms and the SRB would tend to produce uneconomic waste gases including $H_2S$ and $CO_2$. One method of suppressing SRB growth is to degrade the formation hydrocarbons to compounds that are not easily digested by SRBs such as, but not limited to, alcohols, acids, and amine-bearing compounds. Another method is to reduce SRB activity by injecting one or more compounds such as Fe(III) oxide or molybdate into the formation fluids.

Formation Conditions

Environmental conditions in hydrocarbon bearing, subterranean formations may not be conducive to the thriving of indigenous microorganisms. The microorganisms may need to be stimulated to be more active. This stimulation is carried out by modifying one or more parameters of the formation environment. For example, high-salinity environments may greatly slow the rates of hydrocarbon degradation and methanogenesis. Introduction of low salinity waters may stimulate the degradation and methanogenesis activity.

The present invention can be practiced in any hydrocarbon-bearing formation that is suitable for microbial life or that can be modified to be suitable for microbial life. In general, the formation fluids will have a temperature less than about 125° C., a pressure less than about 10,000 psig (6895 kPa), a subsurface pH between about 3 and 10, and a salt concentration less than about 300,000 parts per million.

Formation environmental parameters of principal concern for providing optimal hydrocarbon degradation and methanogenesis conditions include, but are not limited to, temperature, salinity, pH, alkalinity, organic acid concentration, nutrients, vitamins, trace elements, availability of terminal electron acceptors, and toxic substances (to suppress the activity of competing microorganisms). One or more of these environmental parameters may require adjustment or maintenance within specific ranges to initiate or sustain commercial rates of methane generation.

The environmental conditions for promoting growth of a microbial consortium in a formation will necessarily involve many factors including, without limiting the scope of this invention, the following, either alone or in combination:

changes in the formation temperature, pH, Eh, mineralogy, and salinity and the concentrations of $CO_2$, $O_2$, and $H_2$ in the formation; and creation, movement and/or maintenance of boundaries, sometimes referred to as "environmental interfaces", between different hydrocarbon-degradation microbial populations, and/or microbial methanogenesis zones.

Step 3: Modifying the Formation Environment (Adding Stimulants and/or Changing Environmental Factors)

The additions of stimulant(s) or change(s) of environmental factor(s), either alone or in combination, are referred to in this description as microbial growth "stimulants." The particular stimulant, or combination of stimulants, suitable for a particular application will depend on the microorganism consortia to be stimulated and the formation environmental conditions. Since indigenous microorganisms are typically in a nutrient deprived state, one stimulant will typically involve addition of a nutrient. Once a stimulant package is determined, the formation environment can be modified on a continuing basis or discontinued after a suitable period of time to permit growth of the microorganisms.

Injection Process

For growth stimulants that involve injecting a material into the formation, the material can be added to a fluid flood such as an aqueous solution or gas (such as $CO_2$) or solvent or polymer that is injected into the formation by any procedure found most convenient and the invention is not limited to any particular process of introducing the stimulants. The implementation of the present invention will often involve adding the stimulant package by a waterflood program. To simplify the following discussion, the above-identified injection carrier will be referred to as water.

Formation stimulants can be added to water and injected into the formation through one or more injection wells and pressured to flow toward one or more production wells. Underground oil formations are frequently flooded with water in order to supply additional pressure to assist oil recovery. The microbial stimulant is preferably injected into a well as part of the injection program of the waterflood.

The amount of water introduced into the formation and the amounts of microbial stimulants contained in the water will depend upon the results desired. Those skilled in the art can determine the amount needed to provide methane production based on the teachings of this description.

Multiple stimulants can be injected into the formation together or in separate injection steps. For example, a bank of water carrying one stimulant may be followed by a second bank of water carrying a second stimulant. Another example may include injecting one water bank followed by a gas injection step, sometimes referred to as a WAG process.

Creation/Maintenance of Environmental Interfaces

Microorganisms in subterranean formations tend to be most active at environmental boundaries such as between fermentation zones and methanogenesis zones. Therefore, microorganism activity in a formation may be increased by increasing the number of such boundaries, which serve as environmental interfaces. One method for increasing the number of environmental interfaces is to modify the waterflood injection rates. A second method is to alternate or vary the injection stimulants into the formation to in effect create moving environmental fronts. A third method involves forming small-scale environmental interfaces by forming hydrocarbon-water emulsions in the formation or by changing the clay chemistry.

Changing Environmental Conditions

Changing the environmental conditions for promoting growth of microbial consortium in a formation can be accomplished by injection of material into the formation. Environmental factors that can be changed include formation temperature, pH, Eh, and salinity and the concentrations of $CO_2$, $O_2$, and $H_2$ as well as other electron donors and acceptors. As discussed above, the most likely process of environmental change will be by injection of fluids (e.g. water, solvent, and polymer) or gases as part of the secondary or tertiary recovery process.

As an example of changing environmental conditions, oilfield brines often contain high concentrations of inorganic salts that can inhibit or slow growth of microorganisms. Laboratory and field experiments have shown that microorganisms are present in oil formations if the water phase that is present contains salt concentrations are below about 300,000 parts per million. High concentrations of salts tend to favor the growth of special halo-tolerant microorganisms and retard the growth of most microorganisms. Therefore, if the formation contains brines with high salinities, less saline water may be used as the injection fluid to promote stimulation of indigenous microorganisms. Similarly, few microorganisms survive, and fewer thrive at temperatures above about 100° C. to 113° C. Injection of cool water into hotter formations could promote growth of indigenous bacteria by cooling the formation.

Monitoring the Process

During the injection process for stimulating microbial transformation of hydrocarbons to methane, both the formation conditions and the microbial dynamics (ecology) are preferably monitored. This monitoring can be performed in any suitable manner. Normally fluid (for example, hydrocarbon, gas, and water) samples will be obtained from the formation through one or more wells in communication with the formation. The samples are analyzed to determine the concentration and type of microorganisms in the fluid as well as the concentration of stimulants and microbial products in the fluid. Other geochemical analyses may also be performed to assess the effectiveness of the stimulants on the formation environment and to confirm the chemical compatibility of the desired injectant and the subsurface fluids and solids. If based on this monitoring the stimulant effect in the formation is outside the desired range, the concentration of stimulants in the waterflood may be adjusted accordingly to bring the stimulant effect back within acceptable range.

Production

Recovery of methane produced by the microbial activity can be by any suitable gas production technology. The described process is not in any way restricted to secondary or tertiary oil recovery. The process can be used simultaneously with injection of water in secondary oil recovery, at the end of secondary recovery, or at the start of production of an oil field if and when injection of water is found feasible. After introduction of the stimulant package into the formation, the formation may be shut in for a sufficient period of time to allow the microorganisms to produce methane or production may be maintained throughout. The methane may accumulate in a gas zone or gas cap, a free-gas phase overlying a hydrocarbon zone or as an enhanced methane concentration within the original hydrocarbon phase. This gas may be withdrawn through a conventional gas production well that communicates with the gas zone or gas cap. In other formations, the gas may be produced as a product entrained in produced oil and water. In still other formations, the gas may be produced through different zones of wells previously used in production of liquid hydrocarbons from the formation. To enhance microbial gas exsolution (release) from unrecoverable oil and subsequent gas production, it may be beneficial to drop the overall formation pressure by water well production. This invention is not limited by the technology used to recover the methane.

EXAMPLE

Figure 2A:
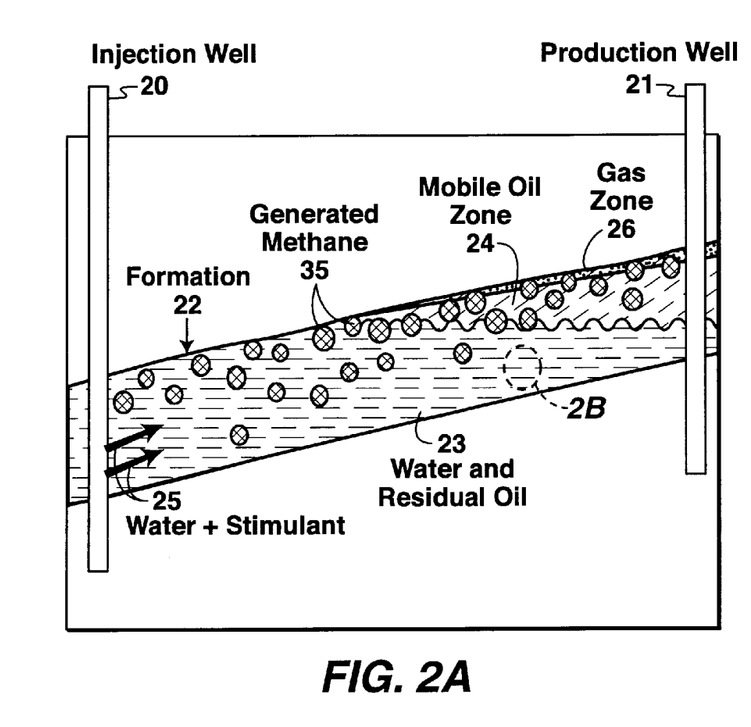
FIG. 2A is an illustrational view of one embodiment of the invention which shows a subterranean hydrocarbon-bearing formation having an injection well and a production well wherein water and a microbial stimulant are injected into the formation to enhance conversion of hydrocarbons to methane.
Figure 2B:
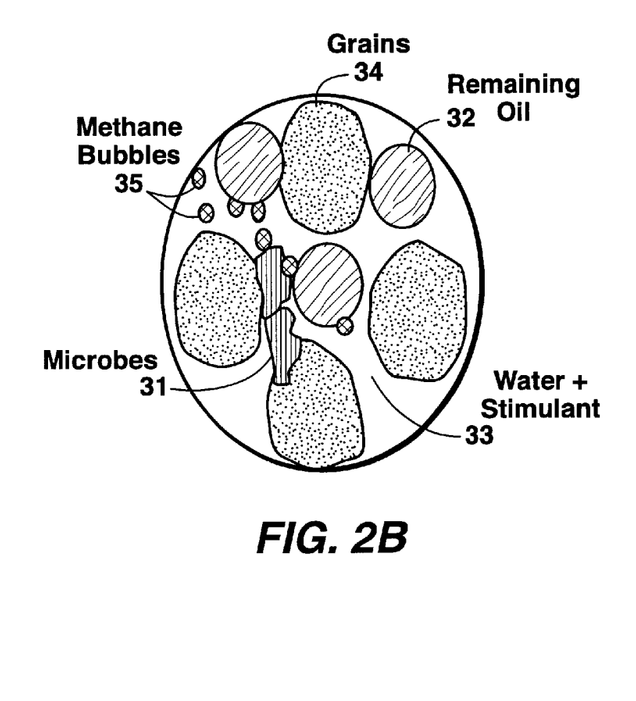
FIG. 2B schematically illustrates an enlargement of the hydrocarbon-bearing formation of the dotted circle 2B of FIG. 2A.

The following field example illustrates a specific procedure for practicing one embodiment of the invention. For this hypothetical example, reference is made to FIG. 2A which illustrates a conventional injection well 20 and production well 21 penetrating a hydrocarbon-bearing formation 22 that contains indigenous microorganisms. The hydrocarbon-bearing formation 22 contains a water and residual oil zone 23 and a mobile oil zone 24. Water (indicated by arrows 25) containing one or more stimulants selected in accordance with the teachings of this description are injected through the injection well 20 into the formation 22. The water containing one or more stimulants enhances or stimulates microbial activity in the pores containing oil to convert at least part of the oil to methane. FIG. 2B, which schematically illustrates an enlargement of the water and residual oil zone 23 of FIG. 2A, shows the distribution of microbes 31, oil 32, water 33, mineral grains 34, and methane bubbles 35 at the pore level. As the subsurface microbes increase the conversion of oil 32 in the pores to methane, the methane concentration (not shown) increases in the fluid phases (water and oil). Eventually the methane concentration may exceed the saturation level in the fluids and form bubbles of methane 35. Referring again to FIG. 2A, the generated methane 35 can migrate to the top of the formation 22 to form a separate gas zone 26 which can flow to the production well 21, or flow as dissolved gas in fluid produced at the production well 21. The methane 35 can for example be dissolved in oil in the mobile oil zone 24 or dissolved in produced water. The methane can also flow as a separate gas phase along with produced oil and water. The methane is recovered at a production well 21 along with produced oil and water.

A person skilled in the art, particularly one having the benefit of the teachings of this patent, will recognize many modifications and variations to the specific embodiments disclosed above. The specifically disclosed embodiments should not be used to limit or restrict the scope of the invention, which is to be determined by the claims below and their equivalents.

What we claim is:

1. A process of stimulating the activity of microbial consortia in a hydrocarbon-bearing, subterranean formation to convert the hydrocarbons to methane, comprising the acts of:
   (a) analyzing one or more components of the formation to determine characteristics of the formation environment;
   (b) detecting the presence of microbial consortia within the formation;
   (c) determining one or more characterizations of one or more microorganisms of the consortia, at least one of the characterizations being of at least one methanogenic microorganism, and comparing the one or more characterizations with at least one known characterization derived from at least one known microorganism having one or more known physiological and ecological characteristics;
   (d) using information obtained from acts (a) and (c) for determining an ecological environment that promotes in situ microbial degradation of hydrocarbons and promotes microbial generation of methane by at least one methanogenic microorganism of the consortia; and
   (e) modifying the formation environment based on the determinations of act (d) to stimulate microbial conversion of hydrocarbons to methane.

2. The process of claim 1 further comprises prior to act (b) the additional act of introducing one or more microorganisms into the formation and allowing the microorganisms to acclimate to the formation environment.

3. The process of claim 1 further comprises, after act (e), the additional act of introducing one or more microorganisms into the formation and allowing the microorganisms to acclimate to the formation environment and repeating acts (a) through (e).

4. The process of claim 1 wherein act (c) comprises (1) identifying a genetic characterization of at least one hydrocarbon-degrading microorganism of the consortia and comparing said characterization with at least one known genetic characterization derived from a known microorganism having one or more known physiological and ecological characteristics and (2) identifying a genetic characterization of at least one methanogenic microorganism of the consortia and comparing said characterization with at least one known genetic characterization derived from a known microorganism having one or more known ecological characteristics.

5. The process of claim 1 wherein the analysis of one or more components of the formation comprises obtaining and analyzing one or more samples of material from the formation, the material comprising at least one of formation water, formation hydrocarbons, or formation solids.

6. The process of claim 5 wherein the analysis of the fluid samples comprises identifying components of the fluids and state values of the fluids in the formation.

7. The process of claim 1 wherein characteristics of the microorganisms of act (c) is determined using a DNA analysis technique.

8. The process of claim 1 wherein identification of methanogenic microorganisms is performed using polymerase chain reaction technology amplifying a portion of methyl reductase genes.

9. The process of claim 1 further comprises determining an ecological environment that promotes in situ degradation of formation hydrocarbons by at least one microorganism of the consortia and promotes generation of methane by at least one methanogenic microorganism of the consortia by growing the identified microorganisms of act (b) in one or more test media containing formation fluid at a selected temperature, pressure and salinity using a multiplicity of growth stimulants.

10. The process of claim 9 wherein the growth stimulants used in the test media comprise at least one of (1) nutrients, (2) electron acceptors, (3) trace elements, (4) buffers, (5) vitamins, (6) catalysts, or (7) combinations thereof.

11. The process of claim 1 further comprises modifying the formation environment by injecting into the formation an aqueous solution containing a microbial stimulant.

12. The process of claim 11 wherein the microbial stimulant comprises at least one of (1) nutrients, (2) electron acceptors, (3) trace elements, (4) buffers, (5) vitamins, (6) catalysts, or (7) combinations thereof.

13. The process of claim 11 wherein the microbial stimulant comprises one or more compounds containing at least one of nitrogen or phosphorus.

14. The process of claim 11 wherein the microbial stimulant is one or more electron acceptors comprising at least one of nitrate, $CO_2$, mineral oxides, humic acid, quinone compounds, sulfate, $Fe^{3+}$, oxygen, or combinations thereof.

15. The process of claim 11 wherein the aqueous solution injected into the formation is fluid flood of a hydrocarbon recovery operation.

16. The process of claim 15 further comprises regulating the injection rate of the fluid flood into the formation in which the formation comprises at least two zones of fluid, each zone of fluid having different fluid densities to create multiple environmental interfaces between at least one formation zone in which hydrocarbon degradation predominates and at least one other formation zone in which methanogenesis predominates.

17. The process of claim 15 further comprises alternating injection of two or more microbial stimulants into the formation.

18. The process of claim 1 further comprising, after modifying the formation environment, shutting in the formation.

19. The process of claim 1 further comprises modifying the formation environment by injecting into the formation an aqueous solution that modifies at least one of formation salinity or formation temperature.

20. The process of claim 1 wherein the modification of the formation environment comprises injecting into the formation a material that changes the concentration of $CO_2$ in the formation.

21. The process of claim 1 wherein the modification of the formation environment comprises injecting into the formation a material that modifies the concentration of $O_2$ in the formation.

22. The process of claim 1 wherein the modification of the formation environment comprises injecting into the formation a material that changes the concentration of $H_2$ in the formation.

23. The process of claim 1 wherein the modification of the formation environment comprises stimulating growth of hydrocarbon-degrading microorganisms in the formation to convert the hydrocarbons to $H_2$ and $CO_2$.

24. The process of claim 1 wherein the modification of the formation environment comprises stimulating growth of hydrocarbon-degrading microorganisms in the formation to convert the hydrocarbons to at least one of alcohols, compounds containing amines, and acids.

25. The process of claim 1 wherein the modification of the formation environment comprises injecting into the formation at least one material that suppresses growth of microorganisms in the formation that compete with the methanogenic microorganisms, thereby promoting growth of methanogenic microorganisms.

26. The process of claim 1 further comprising the act of recovering from the formation methane produced by methanogenic microorganisms.

27. The process of claim 26 wherein the methane recovery is from a gas zone formed by the methane produced by the microorganisms.

28. The process of claim 1 wherein the methane is dissolved in fluid produced at a production well.

29. The process of claim 1 further comprising monitoring formation environment during modification of the formation environment of act (e).

30. The process of claim 1 wherein the hydrocarbon-bearing formation is at least one of peat, lignite, coal, oil shale, oil formation, or tar sands.

31. The process of claim 1 wherein, in addition to methane, the process converts formation hydrocarbons to other low molecular weight hydrocarbons.

32. The process of claim 1 wherein the one or more components of the formation comprises one or more fluids of the formation.

33. The process of claim 1 wherein the one or more components of the formation comprises one or more fluids of the formation and formation rock.

34. The process of claim 1 wherein the hydrocarbons being converted by the microbial action comprise contaminant-hydrocarbons.

35. A process of stimulating the activity of microbial consortia in a hydrocarbon-bearing, subterranean formation to convert formation hydrocarbons to methane, comprising the acts of:

(a) analyzing fluid and rock of the formation to determine characteristics of the formation environment;

(b) detecting the presence of microbial consortia in at least one formation sample;

(c) determining a genetic characterization of at least one hydrocarbon-degrading microorganism consortia, and comparing said genetic characterization with at least one known genetic characterization derived from a known hydrocarbon-degrading microorganism having one or more known physiological and ecological characteristics;

(d) determining a genetic characterization of at least one methanogenic microorganism, and comparing said genetic characterization with at least one known genetic characterization derived from a known methanogenic microorganism having one or more known physiological and ecological characteristics;

(e) using information obtained from acts (a), (c), and (d) for determining an ecological environment that promotes in situ microbial degradation of formation hydrocarbons and promotes microbial generation of methane by at least one methanogenic microorganism of the consortia; and (f) modifying the formation environment based on the determinations of act (d) to stimulate and sustain microbial conversion of formation hydrocarbons to methane.

36. The process of claim 31 further comprising the act of subjecting the formation to a methane recovery means.

37. The process of claim 31 further comprising after act (e) shutting in the formation to allow the microorganisms to convert the hydrocarbons to methane.

* * * * *